(12) United States Patent
Rauniyar et al.

(10) Patent No.: US 12,167,835 B2
(45) Date of Patent: Dec. 17, 2024

(54) DISPOSABLE ENDOSCOPIC DEVICE

(71) Applicant: BOSTON SCIENTIFIC SCIMED, INC., Maple Grove, MN (US)

(72) Inventors: Niraj Prasad Rauniyar, Plymouth, MN (US); Steven T. Carlson, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/947,365

(22) Filed: Jul. 29, 2020

(65) Prior Publication Data

US 2021/0052145 A1   Feb. 25, 2021

Related U.S. Application Data

(60) Provisional application No. 62/890,166, filed on Aug. 22, 2019.

(51) Int. Cl.
*A61B 1/00* (2006.01)
*A61B 1/005* (2006.01)
(Continued)

(52) U.S. Cl.
CPC ...... *A61B 1/00172* (2013.01); *A61B 1/00016* (2013.01); *A61B 1/00032* (2013.01);
(Continued)

(58) Field of Classification Search
CPC ............ A61B 1/00096; A61B 1/00183; A61B 1/0052; A61B 1/0057; A61B 1/015;
(Continued)

(56) References Cited

U.S. PATENT DOCUMENTS 5,179,934 A *   1/1993   Nagayoshi ......... A61B 1/00183
                                          600/152
5,704,898 A     1/1998   Kokish
(Continued)

FOREIGN PATENT DOCUMENTS

CN        105142490 A     12/2015
EP        1 322 214        7/2003
(Continued)

OTHER PUBLICATIONS

Official Communication in European Application No. 20757120.9, dated Feb. 29, 2024 (8 pages).
(Continued)

*Primary Examiner* — Aaron B Fairchild
*Assistant Examiner* — Stephen Floyd London
(74) *Attorney, Agent, or Firm* — Bookoff McAndrews, PLLC

(57) ABSTRACT

An endoscopic device includes a flexible shaft extending distally from a handle which, during use remains outside a living body, the shaft comprising a pull wire extending therethrough from the handle and a distal tip rotatably coupled to a distal end of the shaft, the distal tip comprising an imager directed distally from a distal face of the distal tip, the imager including a chip and a lens, a distal end of the pull wire being coupled to the distal tip in combination with an actuation mechanism coupled to a proximal end of the pull wire so that, actuation of the actuation mechanism, pulls the pull wire proximally through the shaft rotating the distal tip relative to the shaft to alter a field of view of the imager.

18 Claims, 4 Drawing Sheets

(51) Int. Cl.
*A61B 1/05* (2006.01)
*A61B 1/06* (2006.01)

(52) U.S. Cl.
CPC ...... *A61B 1/00096* (2013.01); *A61B 1/00103* (2013.01); *A61B 1/00119* (2013.01); *A61B 1/00183* (2013.01); *A61B 1/005* (2013.01); *A61B 1/0057* (2013.01); *A61B 1/05* (2013.01); *A61B 1/0627* (2022.02); *A61B 1/0676* (2013.01)

(58) Field of Classification Search
CPC ............ A61B 1/05; A61B 2017/00309; A61B 1/0056; A61B 1/0676; G06T 3/0018; G06T 2207/10068; A61M 2025/015; E05D 1/00; E05D 1/04; E05D 1/06
USPC .......................................................... 16/267
See application file for complete search history.

(56) References Cited

U.S. PATENT DOCUMENTS

| | | | |
|---|---|---|---|
| 10,231,719 B2 | 3/2019 | Ranucci et al. | |
| 2001/0018553 A1* | 8/2001 | Krattiger | A61B 1/00183 600/173 |
| 2003/0032863 A1* | 2/2003 | Kazakevich | A61B 1/00105 600/173 |
| 2007/0055103 A1* | 3/2007 | Hoefig | A61B 1/00179 600/137 |
| 2008/0108869 A1* | 5/2008 | Sanders | A61B 1/00124 600/109 |
| 2010/0056861 A1* | 3/2010 | Spivey | A61B 17/00234 600/106 |
| 2012/0197239 A1 | 8/2012 | Smith et al. | |
| 2014/0018732 A1 | 1/2014 | Bagaoisan et al. | |
| 2014/0088361 A1 | 3/2014 | Hrayr et al. | |
| 2014/0243592 A1* | 8/2014 | Kato | A61B 17/00234 600/141 |
| 2014/0320621 A1 | 10/2014 | Sonnenschein et al. | |
| 2015/0032117 A1* | 1/2015 | Kim | A61B 17/3478 606/108 |
| 2015/0359420 A1* | 12/2015 | Hatase | A61B 1/0055 600/110 |
| 2016/0073855 A1 | 3/2016 | Farr et al. | |
| 2016/0367119 A1 | 12/2016 | Ouyang et al. | |
| 2017/0065153 A1* | 3/2017 | Fujitani | A61B 1/00112 |
| 2018/0063387 A1* | 3/2018 | Wei | A61B 1/07 |
| 2019/0216294 A1* | 7/2019 | Matthison-Hansen | A61B 1/0056 |
| 2019/0246884 A1 | 8/2019 | Lu et al. | |
| 2019/0388163 A1* | 12/2019 | Kim | A61B 34/30 |
| 2020/0107898 A1* | 4/2020 | Kim | A61B 34/71 |
| 2020/0254230 A1* | 8/2020 | Sheng | A61M 25/09 |
| 2021/0183025 A1* | 6/2021 | Watson | A61B 1/000094 |

FOREIGN PATENT DOCUMENTS

| | | | |
|---|---|---|---|
| EP | 3 243 426 | 11/2017 | |
| WO | 02/24058 | 3/2002 | |
| WO | WO-2011083217 A2 * | 7/2011 | ......... A61B 1/00183 |
| WO | 2017040692 A1 | 3/2017 | |

OTHER PUBLICATIONS

Schick, A. et al., "3D Measuring in the Field of Endoscopy," Optical Measurement Systems for Industrial Inspection VII, Proceedings of SPIE, vol. 8082, pp. 1-12 (2011).
Office Action in Chinese Application No. 202080059361.7, dated Oct. 24, 2024 (9 pages).

* cited by examiner

DISPOSABLE ENDOSCOPIC DEVICE

PRIORITY CLAIM

The present disclosure claims priority to U.S. Provisional Patent Application Ser. No. 62/890,166 filed Aug. 22, 2019; the disclosure of which is incorporated herewith by reference.

FIELD

The present disclosure relates to an endoscopic device and, in particular, to a disposable endoscope.

BACKGROUND

Urological procedures such as cystoscopy, nephroscopy and hysteroscopy are typically performed using rod-lens systems that utilize a series of lenses in a rigid, semi-rigid or flexible reusable shaft. Such lens systems are expensive and difficult to maintain. Improper sterilization may result in decreased image quality over time, infection in subsequent procedures and an increase in waste chemicals. Rod-lens systems have a fixed camera angle with respect to the distal end of the scope, typically resulting in a need to have multiple scopes available at varying angles. Additionally, valuable space in the scope of rod-lens systems is occupied by the rod lenses themselves.

SUMMARY

The present disclosure relates to an endoscopic device which includes a flexible shaft extending distally from a handle which, during use remains outside a living body, the shaft comprising a pull wire extending therethrough from the handle; a distal tip rotatably coupled to a distal end of the shaft, the distal tip comprising an imager directed distally from a distal face of the distal tip, the imager including an imager chip and a lens, a distal end of the pull wire being coupled to the distal tip; and an actuation mechanism coupled to a proximal end of the pull wire so that, actuation of the actuation mechanism, pulls the pull wire proximally through the shaft rotating the distal tip relative to the shaft to alter a field of view of the imager.

In an embodiment, the lens is a fish eye lens for wide angle viewing.

In an embodiment, the distal tip further comprises a proximal hinge sized and shaped to be coupled rotatably within a cylindrical slot at the distal end of the shaft.

In an embodiment, the distal tip moves laterally relative to a longitudinal axis of the shaft.

In an embodiment, the distal tip further comprises two slanted portions adjacent to a cylindrical portion of the hinge and angled relative to the distal face of the distal tip.

In an embodiment, the shaft further comprises two slanted portions adjacent to the cylindrical slot, the slanted portions being angled relative to a plane perpendicular to a longitudinal axis of the shaft and corresponding to the slanted portions of the distal tip to increase a range of angulation of the distal tip.

In an embodiment, the pull wire extends out of the slanted portions of the shaft via a working channel.

In an embodiment, the working channel is also an irrigation channel.

In an embodiment, the device further includes a light source on the distal face of the distal tip.

In addition, the present disclosure relates to an endoscopic device includes a flexible shaft extending distally from a proximal part that, during use, remains outside a living body, to a distal end, which, during use, is inserted to a target site within the living body, the proximal part including a power connection, the shaft comprising: a fluid channel extending therethrough from a proximal fluid port to a distal end of the shaft; and an imager directed distally from the distal end of the shaft, the imager including an imager chip and a lens, wherein the fluid channel and the imager are molded directly into the shaft.

In an embodiment, the lens is a fisheye lens for wide angle viewing.

In an embodiment, the distal end of the shaft is angled with respect to a longitudinal axis of the shaft.

In an embodiment, the angle of the distal end of the shaft is one of 0-degrees, 30-degrees, and 70-degrees relative to a plane perpendicular to the longitudinal axis.

In an embodiment, the device further includes a battery; and a wireless data transmitter.

In an embodiment, the device further includes a light source on the distal end of the shaft.

Also, the present disclosure relates to a method which includes inserting into a target site within a living body an endoscopic device, the device comprising a handle, a flexible shaft extending distally from a handle and including a pull wire extending therethrough, a distal tip rotatably coupled to a distal end of the shaft, an imager directed distally from a distal face of the distal tip including an imager chip and a lens, and an actuation mechanism coupled to a proximal end of the pull wire; and actuating the actuation mechanism to pull the pull wire proximally through the shaft to rotate the distal tip relative to the shaft to alter a field of view of the imager.

In an embodiment, the lens is a fisheye lens for wide angle viewing, further comprising using an algorithm to correct for distortions caused by the lens.

In an embodiment, the distal tip has slanted portions angled relative to the distal face of the distal tip and the shaft has slanted portions angled relative to a plane perpendicular to a longitudinal axis of the shaft and corresponding to the slanted portions of the distal tip to increase a range of angulation of the distal tip Furthermore, the present disclosure relates to a method comprising inserting into a target site within a living body an endoscopic device, the device comprising a flexible shaft extending distally from a power connection, a fluid channel extending through the shaft from a proximal fluid port to a distal end of the shaft, and an imager directed distally from the distal end of the shaft including an imager chip and a lens, wherein the fluid channel and the imager are molded directly into the shaft; actuating the device to angle the imager to a desired orientation; and transferring, through the power connection, data collected by the imager.

In an embodiment, the method further comprising transferring a fluid from the fluid port, through the fluid channel, to the target site.

BRIEF DESCRIPTION

DETAILED DESCRIPTION

Figure 1:
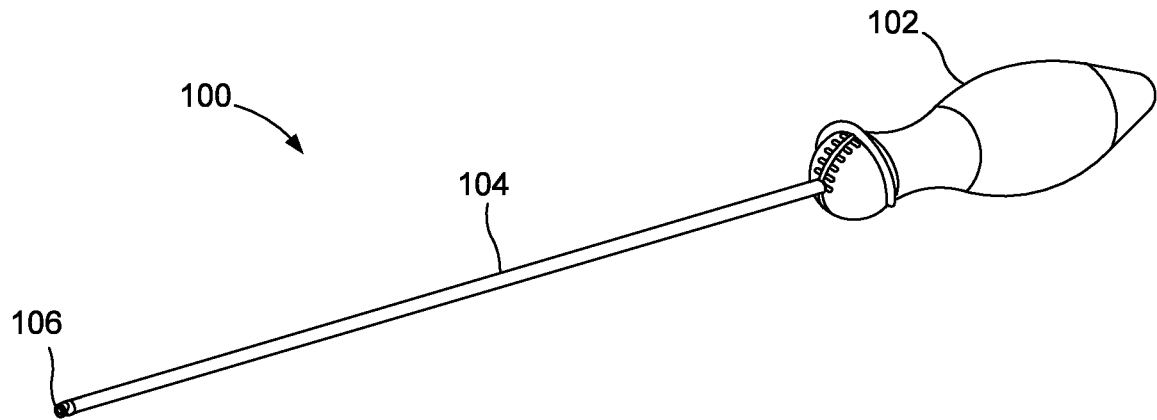
FIG. 1 shows an endoscopic device with an articulating distal tip according to various exemplary embodiments of the present disclosure.

The present disclosure may be further understood with reference to the following description and the appended drawings, wherein like elements are referred to with the same reference numerals. The exemplary embodiments describe endoscopes including a small wafer-based camera chip at the distal tip of the scope, allowing for high resolution imaging with a smaller scope diameter and/or increased space within the scope for other components and/or channels for e.g. irrigation as compared with typical rod-lens systems. The combined lens and chip disposed at the tip of the scope allows for the use of variable angle control, dispensing with the need for multiple scopes of varying angles. The described endoscopes may be disposable or reusable.

The disposable scopes may be manufactured via plastic overmolding over the various camera and/or irrigation components. There are a variety of methods that may be used to protect the chip and lens during the overmolding process. A common method is to make the distal tip and then attach the chip onto that molded or machined distal tip. In such a case, the scope elements such as, e.g., the camera and a light source, may be molded directly into the body of the scope. Extruded plastic or injection molded plastic may also be used for the body of the scopes. Other mechanical, adhesive and soldering methods may be used to join the scope elements and the body of the scope. In another embodiment, reusable scopes may be fashioned from stainless steel hypotube.

FIGS. 1-4 show an endoscopic device 100 with an articulating distal tip 106 according to various exemplary embodiments of the present disclosure. The device 100 includes a proximal handle 102 with an elongated shaft 104 extending therefrom to the distal tip 106. The shaft 104 may be flexible, semi-flexible or rigid. The shaft 104 has at least one longitudinal working channel 114 extending through its length for feeding at least one pull wire 118 therethrough. In the present embodiment the shaft 104 has two working channels 114 and two pull wires 118, however, other configurations may be used as explained in more detail below. An actuation mechanism in the handle 102 for pulling the wire 118 is also explained in more detail below. The distal ends of the pull wires 118 are connected to the distal tip 106 and may be actuated to rotate the distal tip 106 through a range of angles, as shown in FIGS. 3A and 3B.

Figure 2:
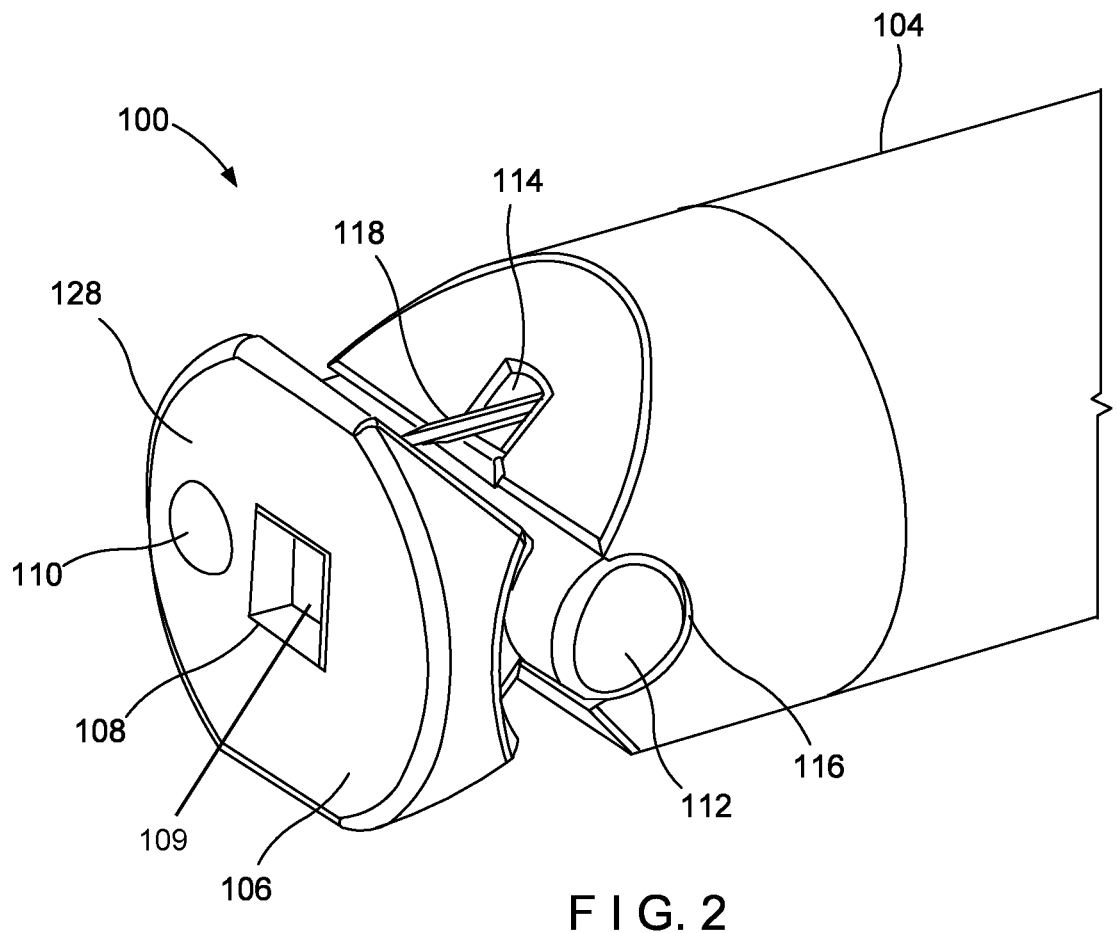
FIG. 2 shows the articulating distal tip of the device of FIG. 1.

As shown in FIG. 2, the distal tip 106 houses a camera assembly 108, a lens 109 positioned within the camera assembly 108 and a light source 110 facing distally out of a flat distal face 128. In the present embodiment the distal tip 106 has a proximal hinge 112 with a cylindrical portion sized to be coupled rotatably within a cylindrical slot 116 at the distal end of the shaft 104. The distal tip 106 has two slanted portions 120 adjacent to the cylindrical portion of the hinge 112, and the shaft 104 has two slanted portions 122 adjacent to the cylindrical slot 116. The pull wires 118 extend out of the slanted portions 122 of the shaft via the working channels 114, with each pull wire 118 connecting to one of the slanted portions 120 of the distal tip 106.

The slanted portions 120 of the distal tip 106 and the slanted portions 122 of the shaft 104 are sized and angled such that the distal tip 106 may articulate within a permitted range of rotation without interference from the shaft 104. Those skilled in the art will ascertain that a variety of ways may be used to join the wire 118 to the distal tip 106. Although in the above embodiment the working channels 114 each contain a pull wire, in another embodiment, the working channels 114 may be used as irrigation channels as well. In another embodiment, the device 100 has the articulating distal tip 106 and the working channels 114, where each of the working channels 114 is an irrigation channel and has the pull wire 118 running through it.

The camera assembly 108 of this embodiment comprises the small wafer-based chip discussed above or any other camera chip of comparable resolution and dimensions. For example, the chip may have a 400×400 pixel resolution, a cross-sectional area of under 1 $mm^2$. The light source 110 may be a single LED, an LED array, or any other suitable light source. The light source 110 may be fiber optic and capable of producing different spectrums and/or intensities of light. Both the camera assembly 108 and the light source 110 may have wiring running through the scope to control mechanisms at the handle 102. Alternately, the camera assembly 108 and/or the light source 110 may include a wireless transceiver at the distal tip 106. The wireless transceiver requires a wire extending from the chip to the handle 102 and a transmitter.

Figure 3A:
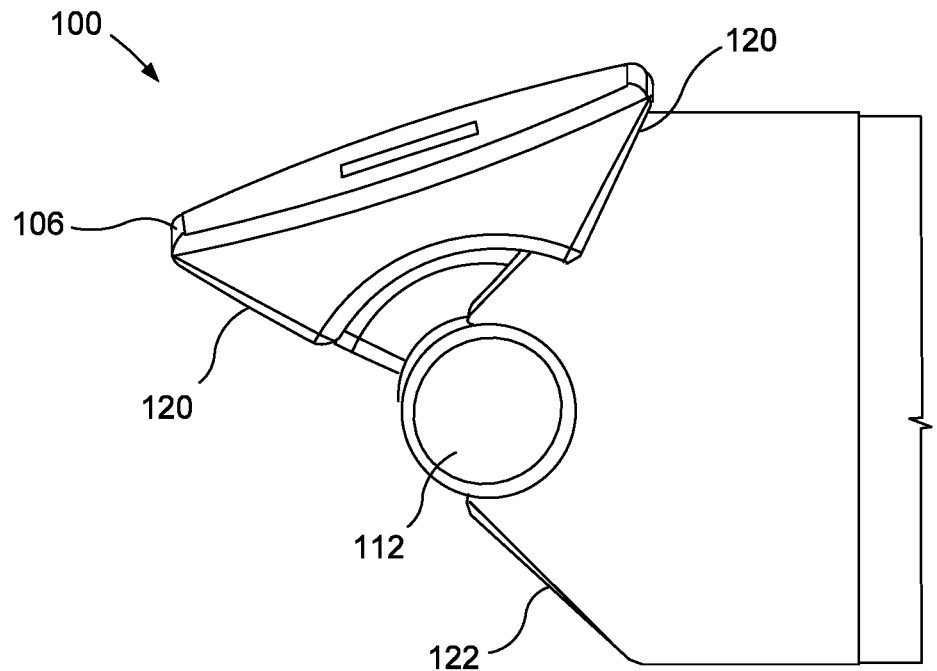
FIGS. 3a-3b show the articulating distal tip of the device of FIG. 1 at varying angles.
Figure 4:
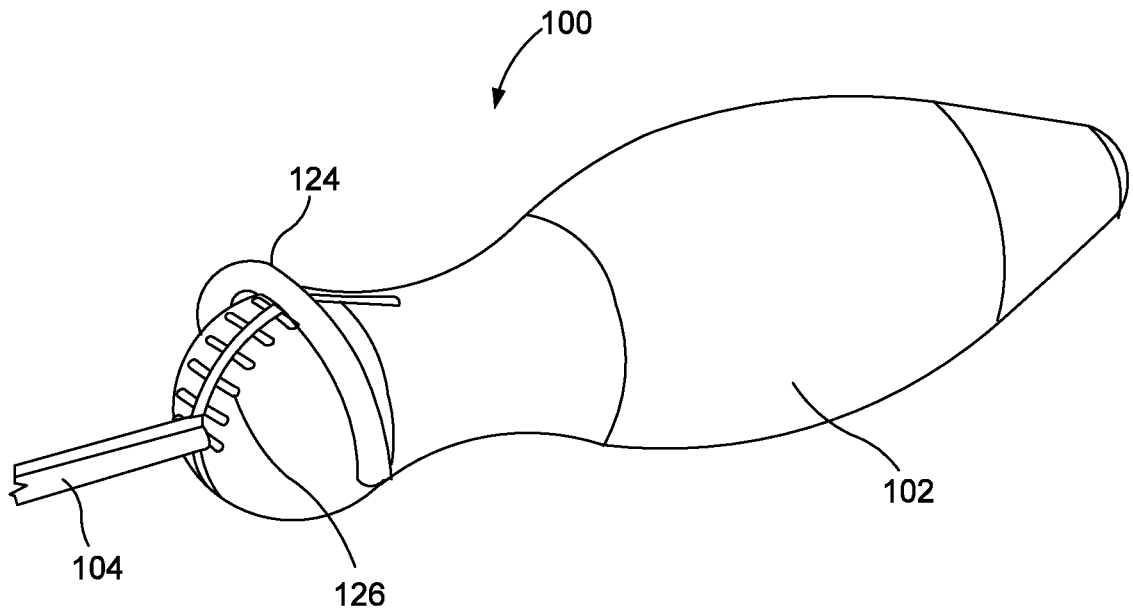
FIG. 4 shows the handle of the device of FIG. 1.

The handle 102 is shaped for ease of gripping during the endoscopic procedure and has an actuator 124 on its distal end for implementing an actuation mechanism internal to the handle 102, as shown in FIG. 4. In the present embodiment the actuator 124 is a simple push/pull ring that is rotatable about a portion of the curved distal end of the handle 102. Rotation of the actuator 124 in a first one of two initial directions, e.g., distally, causes the actuation mechanism to pull a first one of the two pull strings 118, e.g., the top string, proximally, causing the distal tip 106 to rotate upward as seen in FIG. 3A.

Figure 3B:
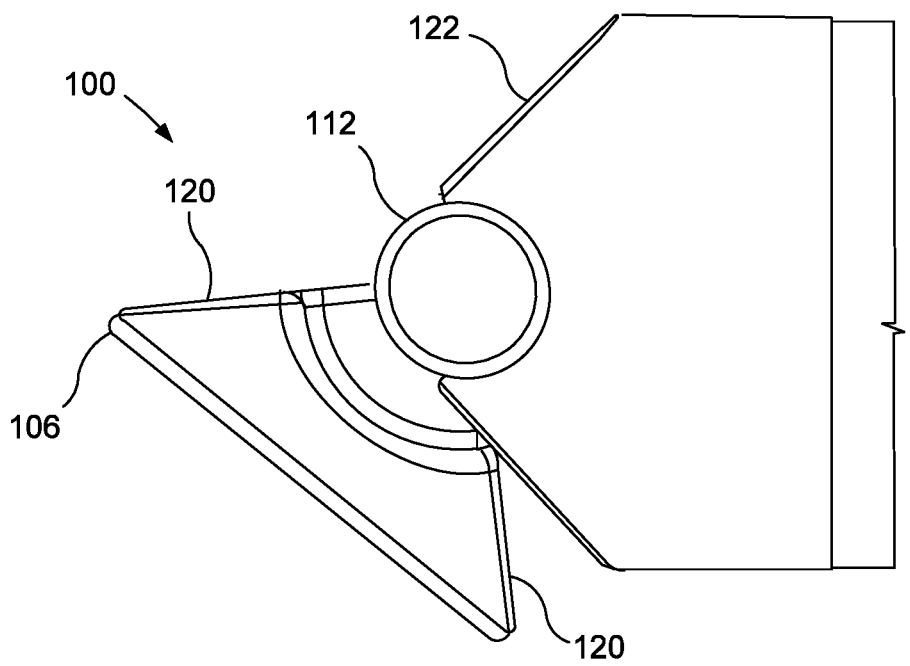

In a similar manner, rotation of the actuator 124 in a second one of the two directions, e.g., proximally, causes the actuation mechanism to pull a second one of the two pull strings 118, e.g., the bottom string, proximally, causing the distal tip 106 to rotate downward as seen in FIG. 3B. The extent of the rotation of the distal tip 106 may be keyed to tip angle indicators 126 represented as a series of distances along the curved distal end of the handle 102. For example, rotation of actuator 124 to a first one of the tip angle indicators 126 may reflect a rotation of the distal tip 106 of 5 deg upward. The angle indicators 126 may provide tactile feedback to the user when a certain angle increment is reached by the distal tip 106. The value of the tip angle at which the tactile feedback is generated may be preset or customizable as would be understood by those skilled in the art.

The present description of the actuator 124 and actuation mechanism is for exemplary purposes only. The actuation of the pull strings 118 may be gear-based, spring-based, or electrical. If the actuation of the pull strings 118 is electrical the handle 102 may not have an actuator built in. Rather, the handle 102 may instead have an electrical port for an external actuator that may be manually manipulated by a touch display or otherwise to trigger the actuation mechanism and pull the pull strings 118. Further, the present description of two pull strings 118 is for exemplary purposes only. In an alternate embodiment, one pull string 118 may be used and connected to one of the two slanted surfaces 120 while a spring mechanism is used on the opposing side or is built into the hinge mechanism.

Figure 5:
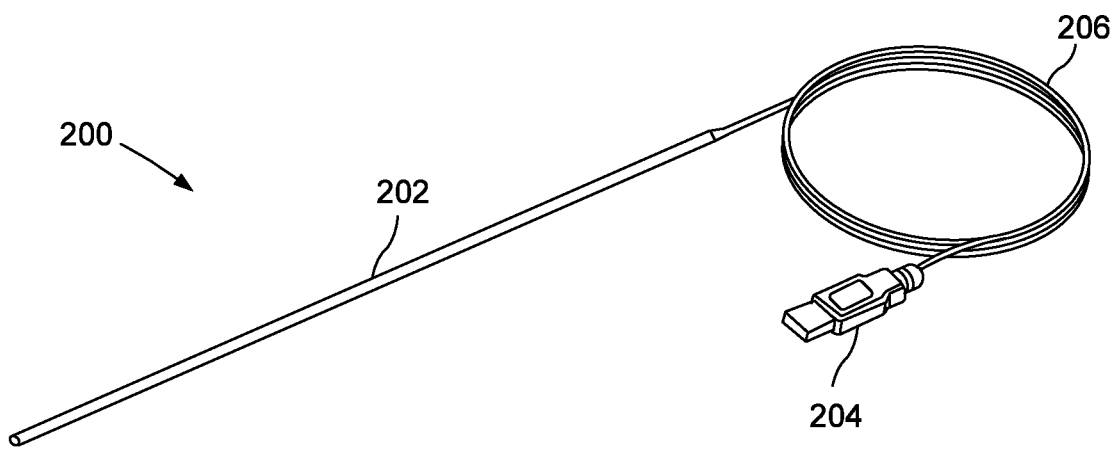
FIG. 5 shows an endoscopic device according to various exemplary embodiments of the present disclosure.
Figure 6:
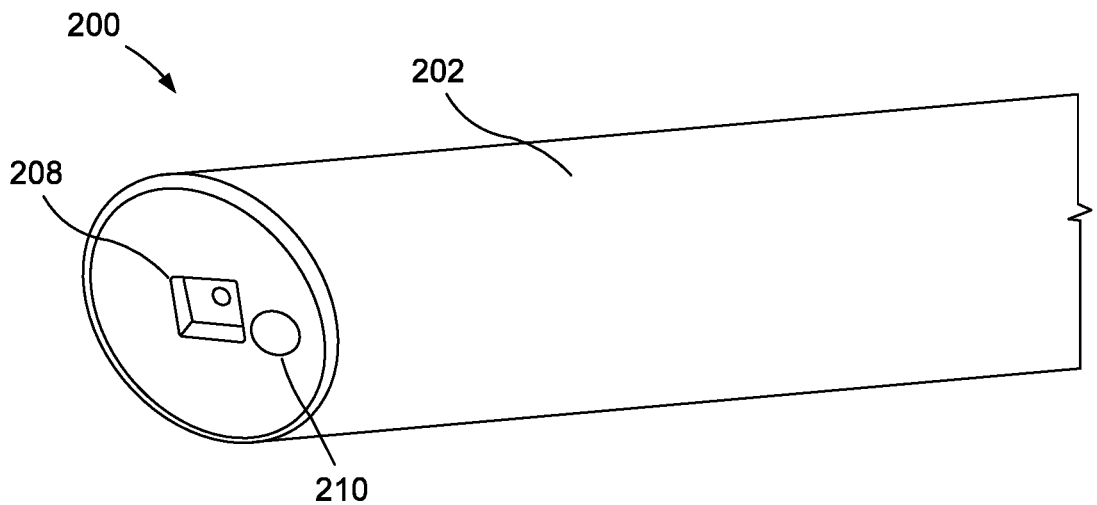
FIG. 6 shows the distal end of the device of FIG. 5.

FIGS. 5-6 show an endoscopic device 200 according to various exemplary embodiments of the present disclosure. The device 200 comprises an elongated overmolded shaft 202 and a connector 204 configured to attach to a scope handle or other suitable equipment so as to transfer data and/or power therebetween. The connector 204 may be, e.g., a USB connector or any custom connector. In an alternate embodiment, a battery and/or wireless data transmitter may be used and forego the need for a connector. The present embodiment shows a cable 206. In an alternate embodiment, the connector 204 may be located at the proximal end of the shaft 202 and forego the need for a cable.

A camera assembly 208, a light source 210 and any associated wiring are molded into the distal end of the shaft 202. In other words, the shaft 202 is molded around the aforementioned elements during the fabrication of the shaft 202 in an overmolding process. The distal end of the shaft may be shaped at an angle with respect to the longitudinal axis of the shaft 202. For example, the angle may be 0 deg, 30 deg or 70 deg. The shaft 202 may be fabricated from, e.g., a rigid or semi-rigid biocompatible plastic. The camera assembly 208 may comprise the small wafer-based chip, similar to the camera assembly 108 of the endoscopic device 100. The light source 210 may be a single LED, an LED array, or any other suitable light source, including a fiber optic light source having an adjustable spectrum and/or intensity of light, similar to the light source 110 of the endoscopic device 100. In the present embodiment the camera assembly 208 and the light source 210 are disposed at the distal end of the shaft 202. However, if the molded material of the shaft 202 is transparent or semi-transparent the light source 210 may be embedded further proximally in the shaft 202.

Figure 7:
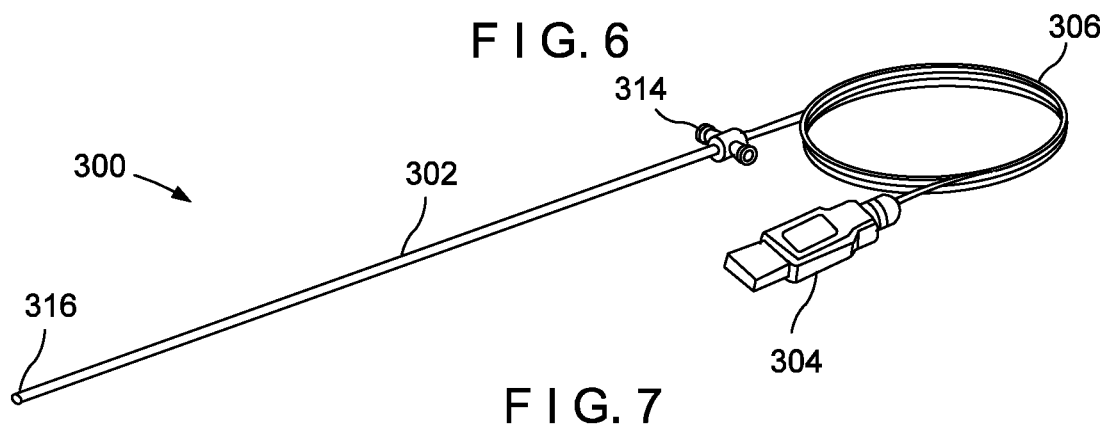
FIG. 7 shows an overmolded endoscopic device having irrigation channels according to various exemplary embodiments of the present disclosure.
Figure 8:
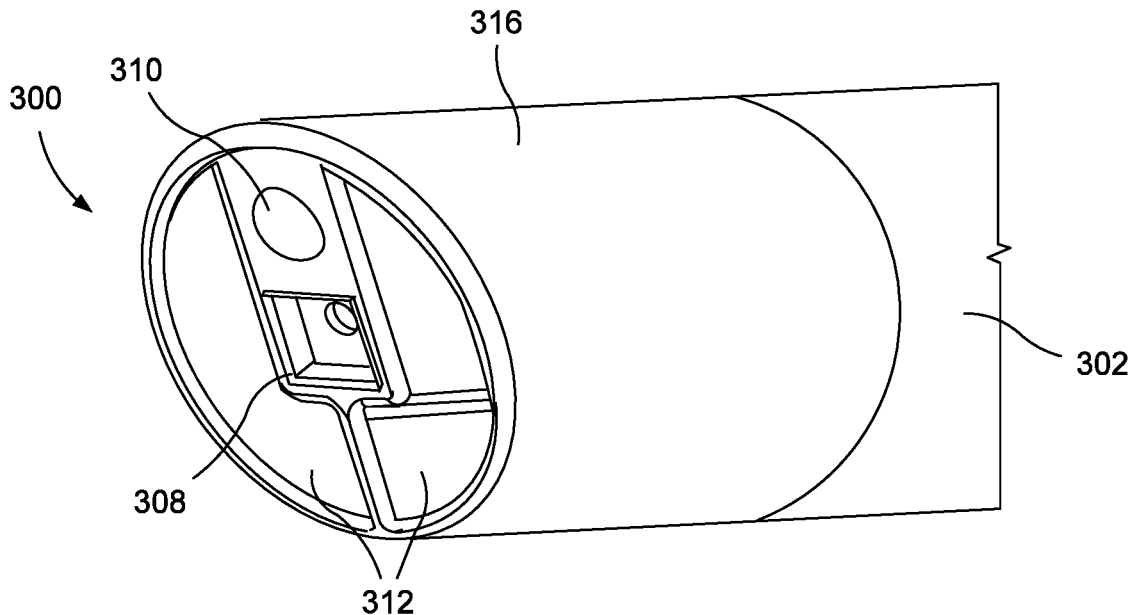
FIG. 8 shows the distal tip of the device of FIG. 7.

FIGS. 7-8 show an overmolded endoscopic device 300 according to various exemplary embodiments of the present disclosure. The device 300 is similar to the device 200 in that various elements are molded into the device during the fabrication of a shaft 302, including a camera assembly 308 and a light source 310. The device 300 may also have a connector 304 and a cable 306, similar to the device 200. However, the device 300 also includes one or more irrigation channels 312 incorporated into the shaft 302.

The present embodiment shows two irrigation channels 312, however, one irrigation channel or more than two irrigation channels may be implemented depending on user requirements. The irrigation channels 312 may be molded directly into the shaft 302 during the fabrication of the shaft 302. In an alternate embodiment, the irrigation channels 312 may be constructed of e.g. steel and the shaft 302 may be molded over the channels 312. The irrigation channels 312 terminate at a port 314 at the proximal end of the shaft 302, the port 314 having a number of tubular connections in proportion to the number of irrigation channels 312, which in the present embodiment is two.

The device 300 has a distal tip 316 that houses the camera assembly 308 and the light source 310. In the present embodiment the tip 316 is fabricated separately from the shaft 302 and is subsequently connected thereto. This arrangement of components allows for a reusable shaft 302 that be fashioned from e.g. steel while the tip 316 is fashioned by the overmolding process discussed previously. However, the shaft 302 and the tip 316 may be fabricated as one piece, in which case the tip 316 will be the distal end of the shaft 316 rather than being connected thereto.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. An endoscopic device, comprising:
 a flexible shaft extending distally from a handle which, during use remains outside a living body, the shaft comprising a pull wire extending therethrough from the handle and a slot at a distal end of the shaft, wherein the slot is cylindrical and extends along an entire width of the distal end of the shaft;
 a distal tip rotatably coupled to the distal end of the shaft, the distal tip comprising a distal face, a distal tip body, and a proximal hinge rotatable within the slot, the distal tip body housing an imager directed distally from the distal face, the imager including an imager chip and a lens, a distal end of the pull wire being coupled directly to the distal tip body, wherein the proximal hinge includes a cylindrical portion sized and shaped to fit within the slot, and wherein the distal tip further comprises two slanted portions adjacent to the cylindrical portion of the proximal hinge and angled relative to the distal face of the distal tip; and
 an actuation mechanism coupled to a proximal end of the pull wire and configured so that, actuation of the actuation mechanism pulls the pull wire proximally through the shaft rotating the distal tip relative to the shaft without moving the shaft to alter a field of view of the imager.

2. The device of claim 1, wherein the lens is a fish eye lens for wide angle viewing.

3. The device of claim 1, wherein the distal tip moves laterally relative to a longitudinal axis of the shaft.

4. The device of claim 1, wherein the further comprises two slanted portions adjacent to the slot, the two slanted portions of the shaft being angled relative to a plane perpendicular to a longitudinal axis of the shaft and corresponding to the two slanted portions of the distal tip to increase a range of angulation of the distal tip.

5. The device of claim 4, wherein the pull wire extends through a working channel of the shaft, out of a first slanted portion of the two slanted portions of the shaft, and to a first slanted portion of the two slanted portions of the distal tip.

6. The device of claim 5, wherein the working channel is also an irrigation channel.

7. The device of claim 5, further comprising:
 a second pull wire extending distally through a second working channel of the shaft, out of a second slanted portion of the two slanted portions of the shaft, and to a second slanted portion of the two slanted portions of the distal tip, and wherein a proximal end of the second pull wire is coupled to the actuation mechanism.

8. The device of claim 7, wherein the second working channel is an irrigation channel.

9. The device of claim 1, further comprising:
 a light source on the distal face of the distal tip.

10. The device of claim 1, wherein the pull wire is longitudinally flexible along a longitudinal axis of the shaft.

11. A method, comprising:
inserting into a target site within a living body an endoscopic device, the device comprising a handle, a flexible shaft extending distally from the handle and including two pull wires extending therethrough, a distal tip rotatably coupled to a distal end of the shaft, the distal tip including a distal face, a distal tip body, two slanted portions angled relative to the distal face, and a proximal hinge, the distal tip body housing an imager directed distally from the distal face of the distal tip including an imager chip and a lens, a first pull wire of the two pull wires being coupled directly to a first slanted portion of the two slanted portions of the distal tip and a second pull wire of the two pull wires being coupled directly to a second slanted portion of the two slanted portions of the distal tip, and an actuation mechanism coupled to the two pull wires; and
actuating the actuation mechanism to pull one of the first pull wire or the second pull wire proximally through the shaft to rotate the distal tip relative to the shaft without moving the shaft to alter a field of view of the imager.

12. The method of claim 11, wherein the lens is a fisheye lens for wide angle viewing, further comprising:
correcting for distortions caused by the lens.

13. The method of claim 11, wherein the shaft has two slanted portions angled relative to a plane perpendicular to a longitudinal axis of the shaft and corresponding to the two slanted portions of the distal tip to increase a range of angulation of the distal tip.

14. The method of claim 13, wherein the two slanted portions of the shaft are adjacent a slot at the distal end of the shaft, and wherein the two slanted portions of the distal tip are adjacent the proximal hinge.

15. The method of claim 11, wherein the shaft further comprises a slot at the distal end of the shaft, and wherein the slot extends along an entire width of the distal end of the shaft.

16. The method of claim 15, wherein the proximal hinge is rotatable within the slot.

17. The method of claim 11, wherein proximal movement of the first pull wire rotates the distal tip in a first direction, wherein proximal movement of the second pull wire rotates the distal tip in a second direction, and wherein the first direction is opposite of the second direction.

18. The method of claim 11, wherein the two pull wires extend within separate working channels of the shaft.

* * * * *